United States Patent
Xu et al.

(10) Patent No.: US 8,447,387 B2
(45) Date of Patent: May 21, 2013

(54) METHOD AND APPARATUS FOR REAL-TIME TUMOR TRACKING BY DETECTING ANNIHILATION GAMMA RAYS FROM LOW ACTIVITY POSITION ISOTOPE FIDUCIAL MARKERS

(76) Inventors: Tong Xu, Ottawa (CA); Jerry Thwin Wong, Irvine, CA (US); Sabee Molloi, Laguna Beach, CA (US)

( * ) Notice: Subject to any disclaimer, the term of this patent is extended or adjusted under 35 U.S.C. 154(b) by 1140 days.

(21) Appl. No.: 11/786,401

(22) Filed: Apr. 10, 2007

(65) Prior Publication Data
US 2007/0265528 A1 Nov. 15, 2007

Related U.S. Application Data

(60) Provisional application No. 60/790,873, filed on Apr. 10, 2006.

(51) Int. Cl.
*A61B 6/12* (2006.01)
(52) U.S. Cl.
USPC ......... 600/436; 250/269.3; 600/426; 600/431
(58) Field of Classification Search
USPC .................. 600/436, 426, 431; 250/269.3
See application file for complete search history.

(56) References Cited

U.S. PATENT DOCUMENTS

| | | | |
|---|---|---|---|
| 6,377,841 B1 * | 4/2002 | Lin et al. | 600/477 |
| 6,484,051 B1 * | 11/2002 | Daniel | 600/436 |
| 7,051,309 B1 * | 5/2006 | Crosetto | 716/122 |
| 7,968,851 B2 * | 6/2011 | Rousso et al. | 250/370.09 |
| 2002/0058057 A1 * | 5/2002 | Kaplan | 424/426 |
| 2003/0036700 A1 * | 2/2003 | Weinberg | 600/436 |
| 2004/0202609 A1 * | 10/2004 | Adair | 424/1.11 |
| 2006/0271300 A1 * | 11/2006 | Welsh et al. | 702/19 |

OTHER PUBLICATIONS

Fayyad et al., Initialization of Iterative Refinement Clustering Algorithms, 1998, American Association for Artificial Intelligence, KDD-98 Proceedings.*
M.A.I. Schutyser et al.: "Numerical Simulation and Pept Measurements of a 3D Conical Helical-Blade Mixer: A High Potential Solids Mixer for Sold-State Fermentation", Biotechnology and Bioengineering, Oct. 5, 2003, vol. 84, No. 1, p. 29-39.
O. Gundogdu and E. Tarcan: "Location-allocation algorithm for multiple particle tracking using Birmingham MWPC positron camera", Nuclear Instruments and Methods in Physics Research A 523 (2004), p. 223-233, Elsevier B.V., www.sciencedirect.com.
O. Gundogdu: "Positron Emission Tomography Particle tracking using cluster analysis", Nuclear Instruments and Methods in Physics Research A 534 Aug. 8, 2004, p. 562-576, Elsevier B.V., www.sciencedirect.com.

(Continued)

*Primary Examiner* — Tse Chen
*Assistant Examiner* — Vani Gupta
(74) *Attorney, Agent, or Firm* — Crowell & Moring LLP

(57) ABSTRACT

Method and apparatus for real-time tracking of a target in a human body. In one embodiment of the invention, positron emission marker may be implanted into a target, the positron emission marker having a low activity positron isotope. In one embodiment, annihilation gamma rays associated with the low activity positron isotope may be detected using a plurality of position-sensitive detectors. In another embodiment, the target may be tracked in real-time based on a position of the positron emission marker.

21 Claims, 11 Drawing Sheets

OTHER PUBLICATIONS

Mari Varjonen: "Three-Dimensional Digital Breast Tomosynthesis in the Early Diagnosis and Detection of Breast Cancer", Susan M. Astley et al. (eds.): IWDM 2006, LNCS 4046, pp. 152-159, 2006. Springer-Verlag Berlin Heidelberg 2006.

C.R. Bemrose et al.: "Application of Positron Emission Tomography to Particulate Flow Measurement in Chemical Engineering Processes", Nuclear Instruments and Methods in Physics Research A 273 (1998), p. 874-880, North-Holland, Amsterdam, Elsevier Science Publishers B.V. (North-Holland Physics Publishing Division).

* cited by examiner

METHOD AND APPARATUS FOR REAL-TIME TUMOR TRACKING BY DETECTING ANNIHILATION GAMMA RAYS FROM LOW ACTIVITY POSITION ISOTOPE FIDUCIAL MARKERS

CROSS REFERENCE TO RELATED APPLICATION

This application claims priority to U.S. Provisional Patent Application Ser. No. 60/790,873 filed on Apr. 10, 2006.

1. Field of the Invention

The present invention relates in general to a method and apparatus for accurate tracking of a target using implanted or embedded positron emission markers.

2. Background

Radiation therapy remains one of the principal modalities for localized treatment of malignant disease. Recently, there have been significant improvements in radiation therapy delivery techniques. Multi-leaf collimator based intensity modulated radiation therapy (IMRT), tomotherapy, intensity modulated arc therapy (IMAT), and robot-based radiosurgery have become available. As compared to conventional 3D conformal therapy (3DCRT), these techniques can significantly improve dose conformity to the planning target volume. Advances in anatomical and functional imaging modalities (CT, MRI, SPECT, PET and US) have led to improved visualization and delineation of tumors. Despite these encouraging advancements, tumor motion due to respiration remains a limiting factor in the delivery accuracy of radiation therapy for pulmonary and abdominal tumors. Studies have shown that upper-abdominal tumors can move as much as 30 mm during respiration. Respiratory gated radiation therapy should be applied to minimize the target volume margin and dose to surrounding normal tissues. Precise respiratory gating requires determining the exact spatial position of the tumor in real-time during treatment. Skin marker and spirometer-based techniques provide indirect indications of tumor position, which can introduce significant tracking errors. Even when the external respiratory surrogates are well correlated with the implanted x-ray fiducial markers prior to each treatment fraction, the residual motion can still be large due to the intra-fractional variation of the patient's breathing pattern.

Real-time tumor tracking can provide accurate respiratory gating or even tumor-tracked radiation therapy. A real-time tumor tracking technique using 1.5-2.0 mm gold markers monitored by two x-ray fluoroscopy systems has been previously reported. However, this technique requires x-ray fluoroscopy throughout the radiation therapy session. The skin dose resulting from x-ray fluoroscopy during real-time tumor tracking can exceed 1 Gray (Gy=J/kg) per hour of treatment time. The fluoroscopy dose is a concern if fluoroscopy based tumor tracking is synchronized with tomotherapy, robot-based radiosurgery, or IMRT using a multileaf collimator. An electronic portal imaging device (EPID) based tumor tracking technique is limited by low image contrast and the possibility that the marker may be outside the radiation field segment. Another reported technique localizes the tumor using implanted wireless electromagnetic transponders. The transponder's large size (1.8×8 mm) makes its application in the lung difficult because of the high incidence of pneumothorax (>35%) with 1.3 mm diameter biopsy needle.

A technique to locate brachytherapy seeds with positron emission tomography (PET) has been proposed by labeling the seed with a positron emission isotope. However, this technique was not designed for real-time tumor tracking, and a conventional PET system can only provide a localization accuracy of approximately 4-5 mm, which is insufficient for tumor tracking.

Accordingly, there is a need in the art for a system and method for real time tumor tracking to overcome one or more of the aforementioned drawbacks.

BRIEF SUMMARY OF THE INVENTION

Disclosed and claimed herein are method and apparatus for real-time tracking of a target in a human body. In one embodiment, a method includes implanting a positron emission marker in the target having a low activity positron isotope. Annihilation gamma rays associated with the isotope are detected using a plurality of position-sensitive detectors. In another embodiment, target position is tracked in real-time based on a position of the positron emission marker.

Other aspects, features, and techniques of the invention will be apparent to one skilled in the relevant art in view of the following detailed description of the invention.

DETAILED DESCRIPTION OF EXEMPLARY EMBODIMENTS

In one embodiment of the invention, tracking of a single particle labeled with a positron emission source may be applied to real-time tumor tracking using implanted positron emission markers. In one embodiment of the invention, a tumor tracking technique may utilize radio-opaque markers filled with a very low activity (30-300 µCi) positron emission source. The positions of the markers may be determined by detecting pairs of annihilation gammas from the positron source using two pairs of position-sensitive gamma detectors mounted on a linear accelerator gantry.

In one embodiment of the invention, a tumor tracking system may utilize positron emission markers and position sensitive gamma ray detectors to localize tumor position in real-time. Radio-opaque markers labeled with a short half-life positron emission source may be implanted inside or around the tumor. In another embodiment, two pairs of position sensitive gamma ray detector modules may be installed on a linear accelerator (linac) gantry at 50-70 cm from the radiation isocenter.

According to another aspect of the invention, a technique may be provided for real-time tumor tracking with low dosage to normal tissue. This technique may increase the feasibility of one or more of precise respiratory gated IMRT, tumor tracked radiation therapy, and robotic motion compensated radiosurgery. In another embodiment of the invention, implantation of positron emission markers may be facilitated using diameters of 0.8 mm or even smaller.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means any of the following: A; B; C; A and B; A and C; B and C; A, B and C. An exception to this definition will occur only when a combination of elements, functions, steps or acts are in some way inherently mutually exclusive.

Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner on one or more embodiments without limitation.

Figure 1:
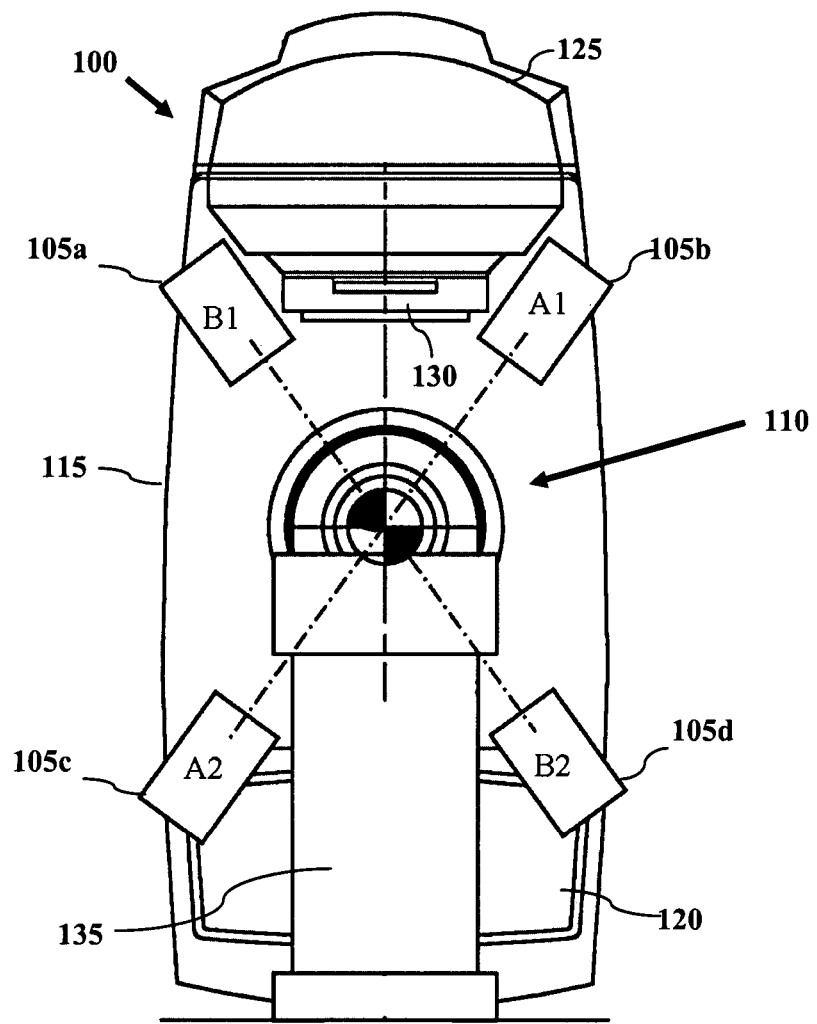
FIG. 1 depicts a tumor tracking system according to one embodiment of the invention.

Referring now to FIG. 1, a tumor tracking system 100 is depicted, which may include a plurality of tumor tracking detectors 105a-105d. In one embodiment, tumor tracking system 100 includes four tumor tracking detector modules 105a-105d mounted on a linear accelerator gantry 115. In one embodiment, detector modules may be mounted 50 cm from the radiation isocenter 110. According to another embodiment, an arrangement of tumor tracking detectors 105a-d may be provided around the linac 125, where detectors 105a and 105b are attached to the sides of the linac head 130, and detectors 105c and 105d are mounted on a linac gantry 135 through an adjustable arm 120, according to one or more aspects of the invention. In one embodiment, the dimensions of the detector modules may be 20×20×30 $cm^3$. The angle between the two detector-pairs may vary from 65 to 90 degrees, depending on the dimensions of linac head. The detector modules may rotate around the patient with the gantry. By acquiring positron annihilation events (i.e., gamma rays) from each marker, the positions of the markers may be determined in real-time with sub-millimeter accuracy. According to one aspect of the invention, the total weight of four tumor tracking detectors may be estimated to be less than 40 kg, which is comparable to current on-line imaging systems mounted on linacs such as the Elekta Synergy® or the Varian Trilogy®. In yet another embodiment, a tumor tracking system may be designed such that the accuracy of gantry rotation or size of the radiation isocenter may not be affected.

According to another aspect of the invention, a tumor tracking system may utilize one or more of isotopes and positron emission fiducial markers. The choice of positron emission isotope may depend on the total treatment time of radiation therapy, which may range from a few days to up to 8 weeks. In one embodiment, potentially useful isotopes may be one of $^{124}$I (t½=4.2 days), $^{74}$As (t½=17.8 days), and $^{84}$Rb (t½=32 days), where $T_{1/2}$ is the isotope half-life.

Figure 2:
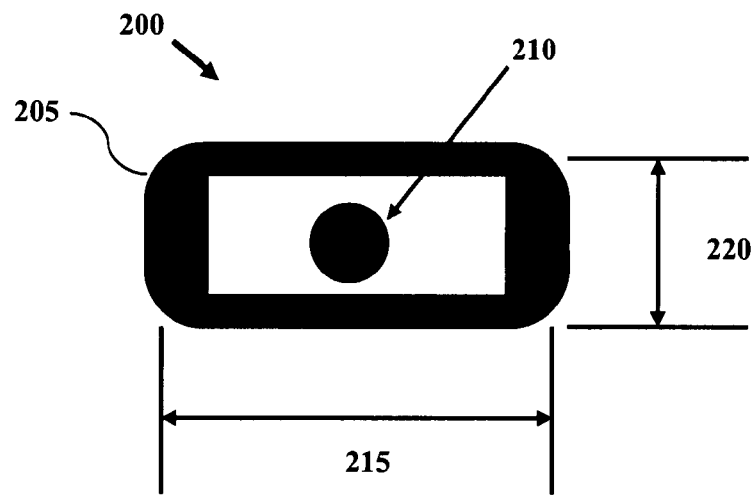
FIG. 2 depicts a positron emission marker capable of carrying out one or more aspects of the invention.

In one embodiment of the invention, tumor tracking markers may be made using techniques for fabricating brachytherapy seeds. Referring to FIG. 2, a marker 200 is depicted according to one embodiment of the invention. The marker 200 may have an overall diameter 220, which may be between 0.5-0.8 mm, and a length 215 between 2-4 mm for easy handling. In one embodiment of the invention, marker 200 may have one of a titanium and a gold capsule 205. According to another aspect of the invention, marker 200 may include a radioactive core 210. The smaller size of tumor tracking markers may be provided for one or more of facilitating implantation and reducing patient risk. It should be note that the dimension and structure of the marker can may according the application. Any markers can be tracked using positron emission tracking technique, as long as it is small (less than approximately 1 mm in diameter) and labeled with positron emission isotopes. For example, the marker can be comprised of a thin gold or titanium wire which is coated with positron emission isotope. Alternatively, the markers may be embedded into the structure of interventional devices or surgical tools for the purpose of tracking these devices or tools.

Figure 3:
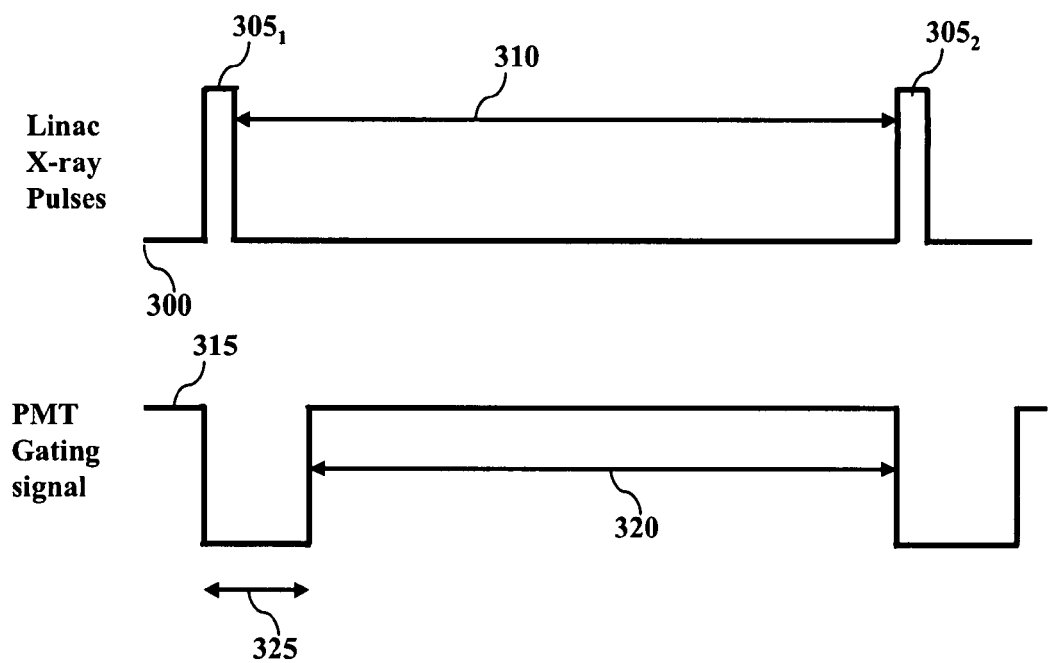
FIG. 3 depicts a timing of a tumor tracking system according to one embodiment.

According to another embodiment of the invention, tumor tracking detectors, may include position sensitive gamma ray detector modules. Gating interface may be required to prevent data acquisition during the linac pulse, as such the linear accelerator may function in a pulsed mode with a pulse rate of 100 to 400 Hz and pulse width of a few micro-seconds. Referring now to FIG. 3, timing of a tumor tracking system according to one embodiment of the invention is depicted. A time interval 310 of 2.5 ms to 10 ms may be provided between consecutive pulses. In one embodiment, tumor tracking detectors may be gated off during each pulse since a signal from the positron emission markers may be much lower than the scatter radiation when a therapy X-ray pulse is on. The photo-multiplier tube (PMT) may be gated off during the Linac x-ray pulses $305_1$ and $305_2$. Linac pulse signal 300 is depicted having time interval 310 between consecutive pulses $305_1$ and $305_2$ according to one embodiment of the invention. PMT gating signal 315 is depicted having a PMT "OFF" period 325 and data acquisition PMT "ON" period 320 according to one or more aspects of the invention. Positron emission data may be acquired during the time interval 320 between pulses with a duty cycle of approximately 80% in order to provide real-time tumor tracking during radiation therapy. In one embodiment, a bismuth germanate (BGO) crystal may be used as a scintillator, due to one or more of high detection efficiency, low afterglow, and relatively low cost of the BGO. Each detector module may be designed to have a field of view (FOV) of 16×16 $cm^2$, which may be sufficient to cover the range of respiratory motion. The BGO crystal may be pixilated and readout by photo-multipliers. In one embodiment of the invention, the intrinsic spatial resolution of the tumor tracking detectors may be between 4-6 mm. The tumor tracking system may achieve sub-millimeter localization accuracy, as the positrons are known to be emitted from point-like markers (active core ~0.4 mm).

According to another embodiment of the invention, a multiple marker tracking algorithm may be provided. In a patient setup, at least 3 fiducial markers may be required to determine both the location and orientation of a tumor accurately. Moreover, multiple fiducial markers may be required to detect marker migration. According to one aspect of the invention, a technique may be provided for tracking more than 3 markers with sub-millimeter precision.

Tracking multiple markers may be complicated by the coincidence-lines arising from K clusters (K>1) that may need to be sorted. Once all the coincidence-lines have been classified according to their respective clusters, the position of each marker may be determined from its set of coincidence-lines. In one embodiment of the invention, sorting of coincidence-lines and pinpointing of marker locations may be based on an Expectation-Maximization clustering algorithm. In another aspect of the invention, the distance from the center of the marker to its annihilation coincidence-lines may follow a Gaussian distribution $G(|\vec{d}(L_n,\vec{m}_k)|,\sigma_k)$, with a zero mean and standard deviation of $\sigma_k$, where k is the cluster index:

$$G\left(\left|\vec{d}\left(L_n, \vec{m}_k\right)\right|, \sigma_k\right) = \frac{1}{\sqrt{2\pi}\,\sigma_k} \exp\left(-\left|\vec{d}\left(L_n, \vec{m}_k\right)\right|^2 / 2\sigma_k^2\right) \quad (1)$$

$\vec{d}(L_i,\vec{m}_k)$ denotes the perpendicular vector connecting the estimated marker location $\vec{m}_k$ to each coincidence-line $L_i$. The $\sigma_k$ corresponds to the intrinsic spatial resolution due to positron range, limited detector resolution, and the non-collinearity of annihilation gammas. Implementation of the Expectation-Maximization algorithm begins (iteration index i=0) with an initial estimate of the source location $\vec{m}_k^{(i=0)}$, standard deviation $\sigma_k^{(i=0)}$, and the relative activity of markers $\alpha_k^{(i=0)}$. The initial standard deviations for all clusters may be set to 5 mm. Moreover, the relative activity of the markers is initially assumed to be evenly distributed:

$$a_k^{(i=0)} = 1/K \text{ with } \sum_{j=1}^{K} a_j = 1 \quad (2)$$

Subsequent iterations i involve performing the following two steps until the estimation of the marker location converges to a point where subsequent adjustment of the marker location changes less than a preset error tolerance, for example 0.05 mm:

a. Expectation step. Compute the probabilities for all coincidence-lines, n=1, ... N, belonging to each cluster, k=1, ... K $$p_{n,k}^{(i)} = \frac{a_k^{(i)} G\left(\left|\vec{d}\left(L_n, \vec{m}_k^{(i)}\right)\right|, \sigma_k^{(i)}\right)}{\sum_{j=1}^{K} a_j^{(i)} G\left(\left|\vec{d}\left(L_n, \vec{m}_j^{(i)}\right)\right|, \sigma_j^{(i)}\right)} \quad (3)$$

b. Maximization step. Update parameters $\alpha_k, \vec{m}_k, \sigma_k, k=1, \ldots K$ $$a_k^{(i+1)} = \frac{\sum_{n=1}^{N} p_{n,k}^{(i)}}{N}; \quad (4)$$

$$\sigma_k^{(i+1)} = \frac{\sum_{n=1}^{N} p_{n,k}^{(i)} \cdot \left|\vec{d}\left(L_n, \vec{m}_k^{(i)}\right)\right|^2}{\sum_{n=1}^{N} p_{n,k}^{(i)}}; \quad (5)$$

$$\vec{m}_k^{(i+1)} = \vec{m}_k^{(i)} + \vec{V}_k \quad (6)$$

$\vec{V}_k^{(i)}$ denotes the adjustment vector for each previously estimated marker position required to minimize the RMS distance of the marker to the coincidence-lines that belong to it:

$$\vec{V}_k^{(i)} = \frac{\sum_{n=1}^{N} p_{n,k}^{(i)} \cdot \vec{d}\left(L_n, \vec{m}_k^{(i)}\right)}{\sum_{n=1}^{N} p_{n,k}^{(i)}} \quad (7)$$

Due to scatter and random coincidence, corrupted coincidence lines may introduce significant errors to marker localization. In order to minimize errors introduced by the corrupted coincidence lines, only coincidence lines that are within $2\sigma_k^{(i)}$ from a marker's position $\vec{m}_k^{(i)}$ are allowed to contribute to the update of the marker's position. The probability of a coincidence line $L_n$ will be set to zero for cluster k if $|\vec{d}(L_n,\vec{m}_k^{(i)})|>2\sigma_k^{(i)}$.

To test the tumor tracking system, a Monte Carlo simulation model was used, wherein the radiation dose to surrounding tissues resulting from the positron emission markers was investigated as well as the localization accuracy and feasibility of locating more than one marker. A Monte Carlo simulation package (GEometry ANd Tracking 4) for radiation transport was used for this purpose. A water cylinder with a 30 cm diameter and 60 cm length was placed at the radiation isocenter of a linac to simulate a patient. Two pairs of detector modules were positioned 50 cm from the radiation isocenter (e.g., radiation isocenter 110 of FIG. 1). For the aforementioned test, each detector module consisted of an array of 40×40 BGO crystals. Each crystal used in the test, included dimensions of 4×4×30 mm³. The positron emission marker was modeled as an active 0.4 mm spherical core with a 0.2 mm thick gold shell. The radioactive isotope was uniformly distributed inside the core. GEANT4's radioactive decay module was used to simulate the radioactive decay of isotopes. The non-collinearity between the two annihilation gammas is an important factor that affects spatial resolution. The non-collinearity angle was simulated by a Gaussian distribution with 10 mRadian (mR) FWHM. The detector energy resolution may be 25% FWHM for a 511 keV gamma. The energy window may be set to 420-600 keV.

In the simulation model above, non-zero energy deposition in the BGO crystal will trigger an event. The center of mass of the energy deposition will be recorded with a spatial resolution that equals the crystal pitch (4 mm). It is assumed that an event may be considered valid if the following two conditions are met:

a. There are two coincident hits, and the detected energies fall within the energy window (420-600 keV)

b. The coincident hits are detected by the detector pair A1 and A2 or detector pair B1 and B2 (see FIG. 1).

Each valid event will form a coincidence line for localization.

In order to evaluate a multiple marker localization algorithm of one embodiment of the invention, four markers labeled with $^{124}$I were considered in the Monte Carlo simulation. The positions (in mm) of the 4 markers were: (0,0,0), (15,0,0), (0, 20,0), (0,0,20). Lines that connect two coincident hit positions were recorded as detected coincidence lines used for localization. In total, 370 million $^{124}$I decays from the four markers were simulated and about 80 thousand coincidence lines were obtained. The algorithm was tested with different sizes of coincidence line collections. Acquired coincidence lines were divided into many coincidence line collections; the size of collection varied from 50-1000 coincidence lines. One coincidence line collection was used as the input for each execution (run) of the algorithm. It was found that the initial estimate of the marker position and the number of coincidence lines affected the performance of the clustering algorithm. In a clinical application, the error in initial estimation may arise from one or more of patient setup, respiration, and marker migration. During the evaluation of the algorithm, the initial estimation error was simulated by generating random initial positions. These initial positions were randomly and uniformly distributed around the known true position of each marker with a preset random range, for example ±10 mm. The algorithm was evaluated with three different initial estimation error ranges (±5 mm, ±10 mm, and ±15 mm) and a range of coincidence line collections (50-1000). One thousand localization runs were performed for each setup. Because each run will have a different random initial position, the 80 thousands coincidence lines can be reused during these 1000 runs. Localization error may be defined as the distance between the position determined by the algorithm and the true location. A marker may be considered successful if it is localized within 2 mm distance from its true location. A localization run is considered as successful if all the four markers are successful. For each evaluation setup, the localization accuracy was determined as the average error among all the successful markers.

In a simulation study, an unsuccessfully localized marker may be identified by its distance to the true position of the marker. However, the true position is unknown in real applications. A method of identifying markers that have been localized incorrectly by the algorithm (i.e. failed markers) is required. The coordinate of a failed marker may arise from a collection of coincident lines that come from more than one marker. As a result, the cluster standard deviation $\sigma_k$ (Eqs. 1 and 5) may correlate with the localization error. The $\sigma_k$ was recorded to investigate this hypothesis.

According to one aspect of the invention, the coincidence count rate and scatter fraction may be calculated from 1 million decay events for a marker at the radiation isocenter. The following table provides exemplary values of the coincidence count rate and scatter fraction calculated from 1 million decay events for a marker at the radiation isocenter with a patient thickness equal to 30 cm according to one embodiment of the invention.

TABLE 1

| | Isotope | | |
|---|---|---|---|
| | $^{124}$I | $^{74}$As | $^{84}$Rb |
| Total coincidence event/1M decay | 247 | 318 | 255 |
| events with scattered annihilation gamma | 29 | 32 | 40 |
| scatter from non annihilation gammas | 2 | 6 | 2 |
| Total scatter fraction | 0.12 | 0.12 | 0.16 |
| Sensitivity: coincidence count/sec/(100 μCi)) | 913 | 1177 | 943 |
| Coincidence counts/100 ms with 80% data acquisition duty cycle | 73 | 94 | 75 |

Figure 4:
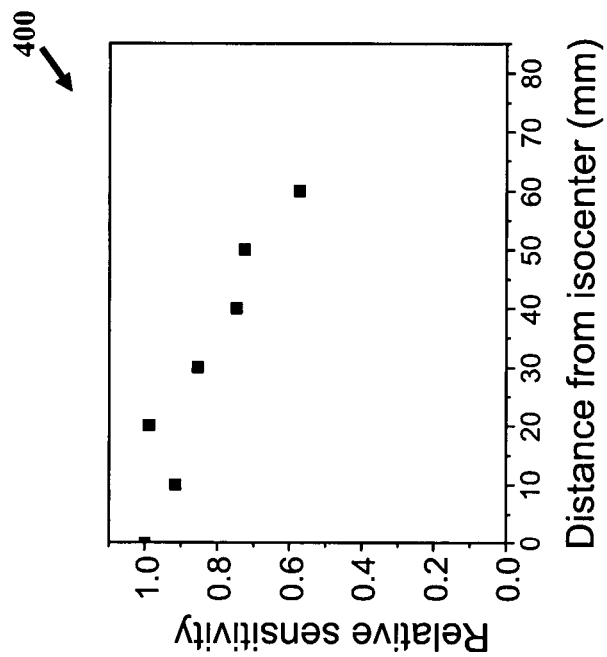
FIG. 4 depicts the relative sensitivity of a tumor tracking system versus distance from a radiation isocenter according to one or more aspects of the invention.

Referring to the Table 1 above, the results demonstrate that approximately 80 coincident events may be acquired within 100 ms. This may be sufficient to provide accurate localization. Referring now to FIG. 4, the relative sensitivity of an exemplary tumor tracking system (16×16 cm$^2$ FOV), is depicted by graph 400 as a function of distance from the radiation isocenter according to one embodiment of the invention. The sensitivity may be reduced to 55% near the edge of the FOV. This may indicate that higher activity is required if a marker is located close to the edge of the FOV.

Figure 5B:
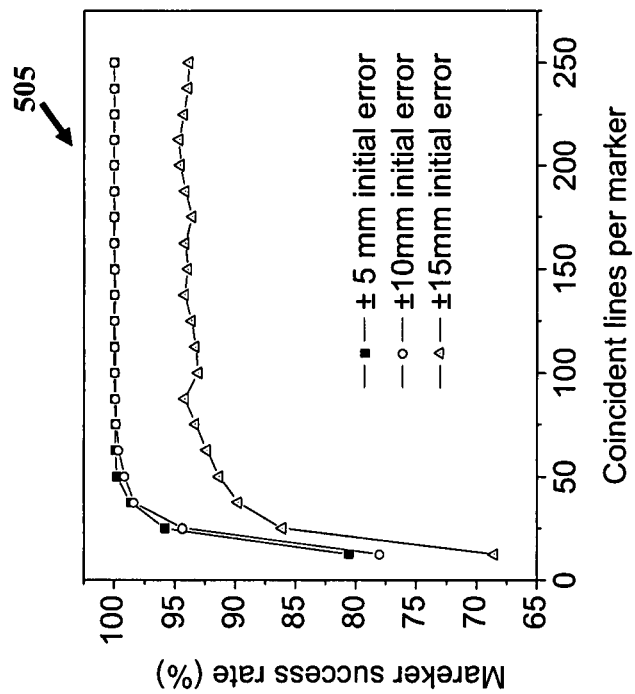
FIGS. 5A-B depict success rates versus coincident lines per marker according to one embodiment.
Figure 5A:
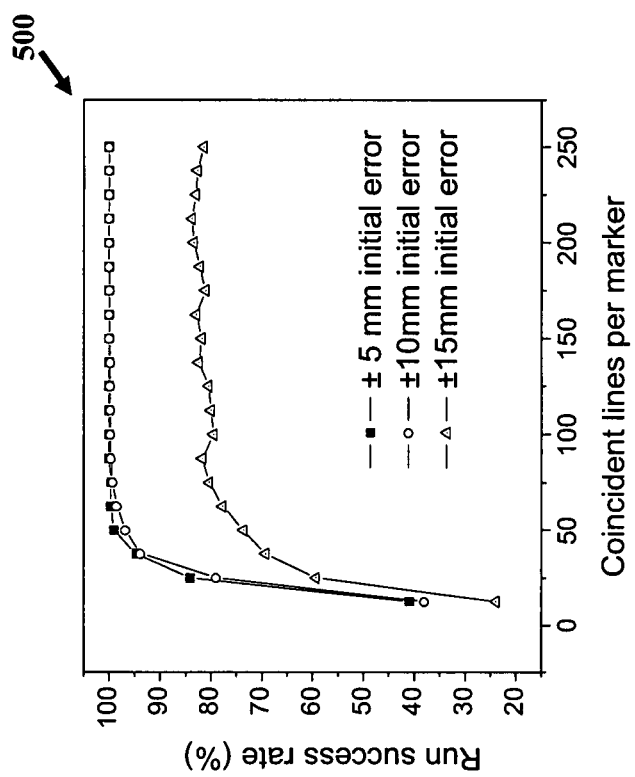

Referring to FIGS. 5A-5B, results of a Monte Carlo simulation of multiple marker localization according to one embodiment of the invention is depicted. Referring to FIG. 5A, graph 500 shows how the run success rate increases with the size of coincidence line collection used for localization, but decreases with initial error according to one embodiment of the invention. Run success rates of 99.7% and 98.5% may be achieved with approximately 62 coincidence lines per marker with initial error ranges of ±5 and ±10 mm, respectively. In one embodiment, the number of coincidence lines may be acquired from 100 μCi markers in 100 ms (30 cm patient thickness). For an initial error range of ±15 mm, which is comparable to a distance of 15-20 mm between markers, the run success rate is 77.7% with 62 coincidence-lines per marker. Referring now to FIG. 5B, graph 505 illustrates the marker success rate as a function of coincidental lines per marker. Marker success percentages of 99.9%, 99.6%, and 92.4% for ±5 mm, ±10 mm, and ±15 mm initial errors, respectively, may be depicted according to one or more aspects of the invention. The marker success percentages may be higher than the run success rates because most of the failed runs may only incorrectly localize one marker. Provided in table 2 are statistics on runs with different numbers of successful markers. An average of 62 coincidence-lines per marker were used for each run (4 markers per run) and a total of 1000 runs were evaluated.

TABLE 2

| | | Initial error range | | |
|---|---|---|---|---|
| | | ±5 mm | ±10 mm | ±15 mm |
| Number of runs with different # of successful markers | All 4 markers are successful | 997 | 985 | 777 |
| | 3 markers are successful | 3 | 15 | 144 |
| | 2 markers are successful | 0 | 0 | 75 |
| | 1 marker is successful | 0 | 0 | 4 |
| | All 4 markers failed | 0 | 0 | 0 |

Table 2 indicates that, with a ±15 mm initial error range, there were 223 failed runs and 144 of them only failed one out of four markers. In clinical operation, these failed markers can be identified and recovered so that the delivery accuracy may not be degraded.

Figure 6:
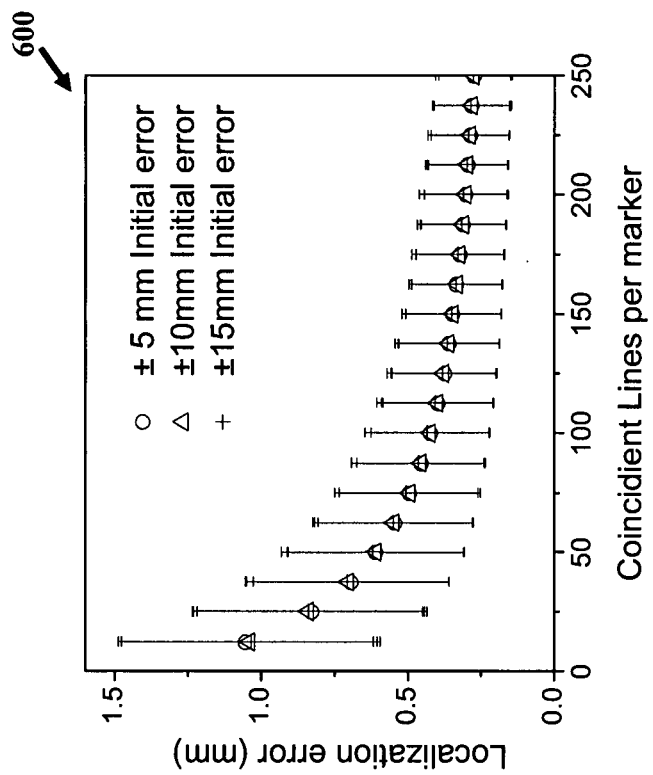
FIG. 6 depicts average localization error versus the average number of coincidence lines per marker according to one or more aspects of the invention.

Referring now to FIG. 6, a plot 600 of average localization error among successful markers (error <2 mm) as a function of the size of coincidence line collection is depicted according to one or more aspects of the invention. The standard deviation in the localization error may be represented by the error bars. The three different initial error ranges did not show any visible differences in the localization accuracy of successful markers. FIG. 6 may also indicate that localization accuracy improves with the size of coincidence line collection. According to one aspect of the invention, with an average of 62 coincidence lines per marker, the localization error is 0.55(±0.27) mm.

Figure 7:
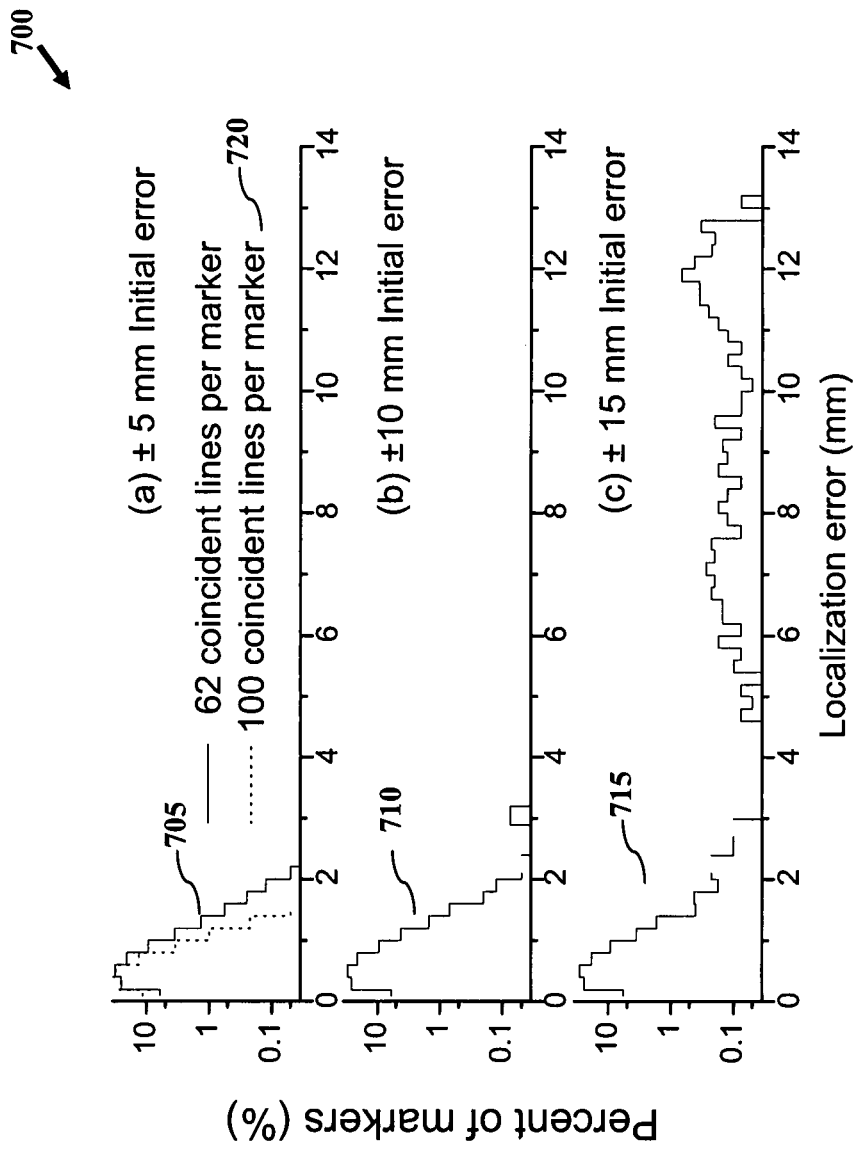
FIG. 7 represents the distribution of localization error at different initial error estimation ranges according to one embodiment.

Referring to FIG. 7, a histogram distribution 700 of localization error for the three initialization ranges 705, 710 and 715 using 62 coincidence lines per marker is depicted according to one embodiment of the invention. FIG. 7 depicts distributions 705, 710 and 715, which may be almost identical for errors less than 3 mm, which may be consistent with the overlapping averages and standard deviations will be depicted in FIG. 8 below. A distribution of errors less than 3 mm may determined by the inherent spatial resolution of the tumor tracking system and number of coincident lines used for localization. Referring to FIG. 7A, the dashed line 720 may be depict that both the mean and standard deviation in localization error can be reduced by increasing the number of coincident lines collected from 62 to 100. However, the distribution for initialization errors of 15 mm shows that a few percent of its markers may have very large errors. Most of these markers may be identified by the cluster standard deviation (see Eq. 1).

Figure 8:
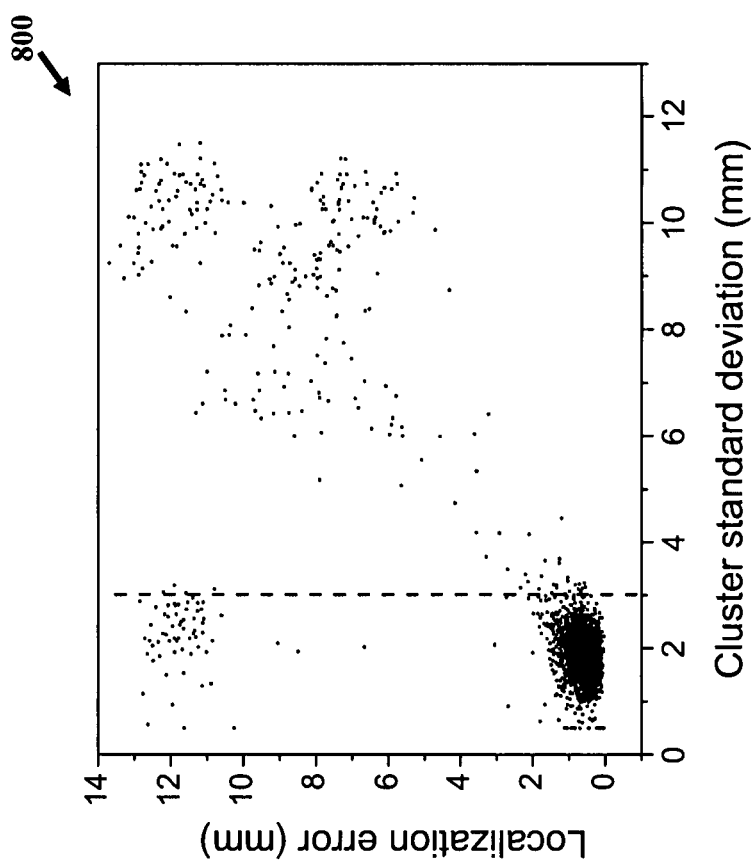
FIG. 8 depicts simulated localization error plotted against cluster standard deviation according to one or more aspects of the invention.
Figure 9:
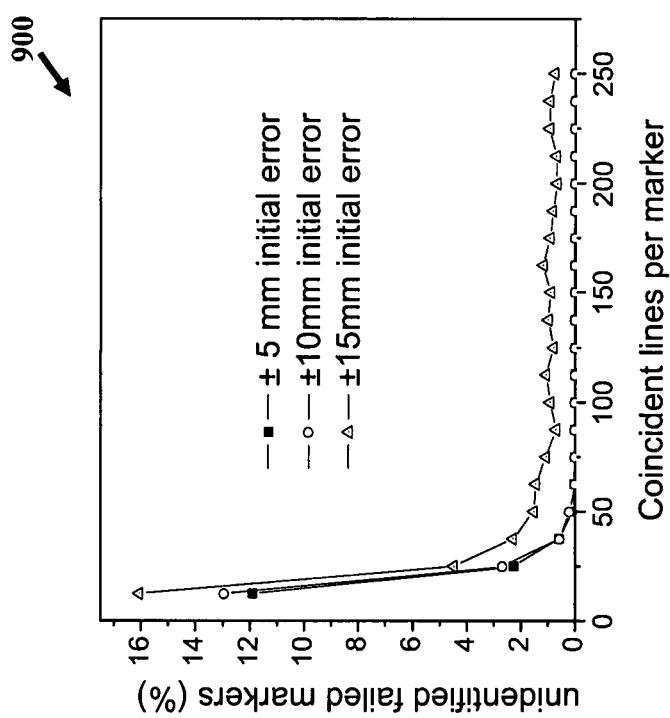
FIG. 9 represents unidentified failed markers as a function of initial error according to one embodiment.

Referring now to FIG. 8, graph 800 shows the localization error from the true location versus $\sigma_k$, according to one embodiment of the invention. These data points comprising graph 800 may be obtained when an initial error range may be ±15 mm and the coincidence line collection size is 250 (average of 62 coincidence lines/marker). In one embodiment of FIG. 8, a total of 4000 marker localizations as depicted. These data points may be distinctly separated into three groups. A $\sigma_k$ less than 3 mm almost always corresponds to a small localization error (less than 2 mm). Thus a threshold of 3 mm on $\sigma_k$ may be sufficient to identify most failed markers. FIG. 8 depicts markers localized with small $\sigma_k$, but with very large errors. These failed markers cannot be identified using $\sigma_k$. Referring now to FIG. 9, graph 900 depicts the percentage of unidentified failed markers, relative to the total number (4000) of marker being localized, as a function of initial error and number of coincidence lines per marker used for localization is depicted according to one or more aspects of the invention. With an initial error below 10 mm, all failed markers may be identified when more than 62 coincident lines per marker are used for localization. With the initial error at 15 mm, about 1% of markers were incorrectly localized and unidentified as failed markers.

In one embodiment of the invention, the computation time for each run may be about 20 ms with an initial error within 10 mm and using a total of 400 coincidence lines per run (100 per marker) (Pentium 4, 2.8G processor, 512 MB memory). This speed may be sufficient for real-time localization at 30 samples per seconds.

Figure 10:
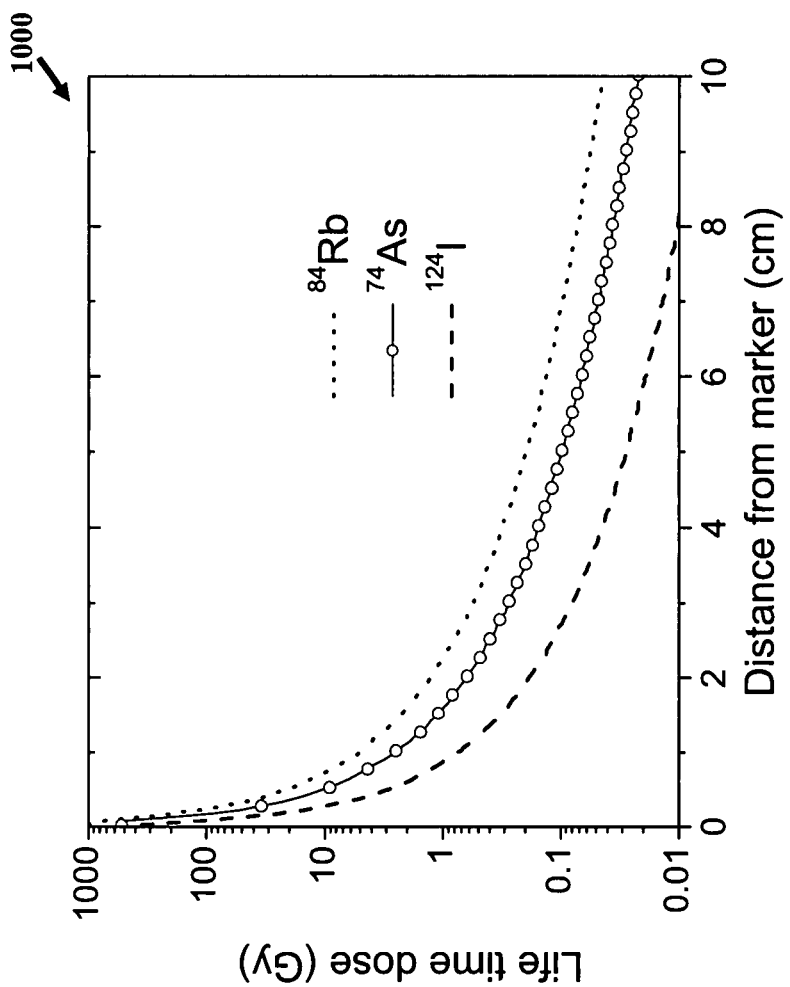
FIG. 10 depicts life time dose from markers with different isotopes as a function of distance according to one or more aspects of the invention.

Referring to FIG. 10, graph 1000 illustrates the life-time dose distribution versus the distance from the center of the marker, is depicted according to one embodiment of the invention. The dose decreases rapidly with increasing distance. Provided in Table 3 are the total life-time dose from 100 μCi markers at 5, 10, and 15 mm from the center of the marker.

TABLE 3

|  | Isotope | | |
| --- | --- | --- | --- |
|  | $^{124}$I | $^{74}$As | $^{84}$Rb |
| Half-life (days) | 4.2 | 18 | 32 |
| Activity (μCi) | 100 | 100 | 100 |
| Total dose (Gy) @ 5 mm (affected volume: 0.5 cc) | 2.6 | 9.0 | 18.6 |
| Total dose (Gy) @ 10 mm (affected volume: 4.2 cc) | 0.7 | 2.46 | 4.96 |
| Total dose (Gy) @ 15 mm (affected volume: 14 cc) | 0.32 | 1.09 | 2.24 |

Regarding linac induced background estimation, a detector may be gated to avoid detecting scattered radiation from the linac. However, it is well known that an x-ray beam with energy higher than 10 MV will create induced background radiation due to photo-nuclear reactions. The induced background radiation exists even when the linac x-ray is off.

Table 4 provides estimation of random coincidence rates in two pairs of 16×16 cm² tumor tracking detectors from induced photon background after the delivery of 1000 MU from an 18 MV photon beam according to one or more aspects of the invention.

TABLE 4

| Isotope | Half-life (minutes) | Gamma energy (keV) | Air exposure rate mR/h after 1000 MU | Counts/sec on 16 × 16 cm² detector | Total random coincidences/sec |
| --- | --- | --- | --- | --- | --- |
| $^{28}$Al | 2.3 | 1779 | 1.0 | 56k | N/A |
| $^{62}$Cu | 9.7 | 511 | 0.5 | 130k | 360 |
| $^{187}$W | 1422 | 479, 686 | 0.01 | 2.6k |  |

The dose deposited within 5 mm around the positron marker is 9.0 Gy (or 2.6 Gy) with 100 μCi $^{74}$As (or $^{124}$I). The dose decreases to approximately 2.46 Gy (0.7 Gy for $^{124}$I) at 10 mm from the marker.

Figures 11A, 11B:
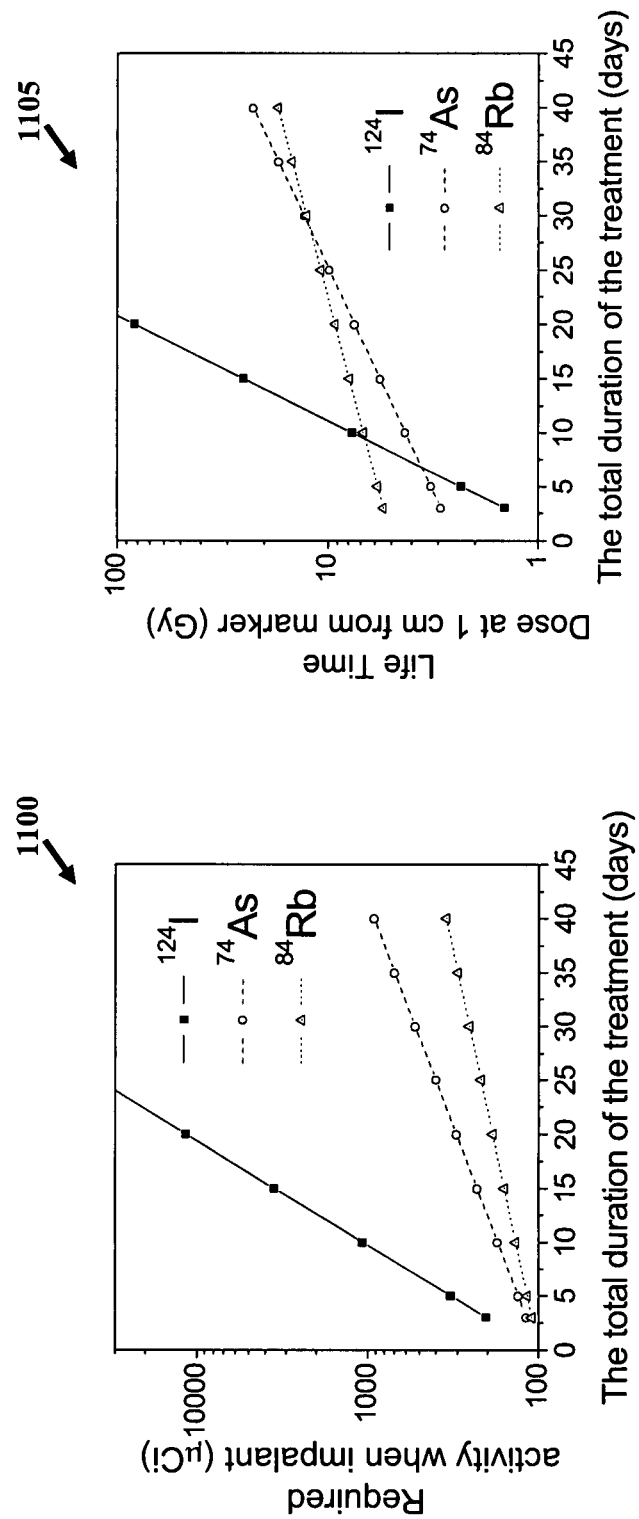
FIGS. 11A-B represent required marker activity at the time of implantation and the total life dose at 1 cm from a marker according to one embodiment.

The dose may depend on marker activity at the time of implantation. As described above, the algorithm may achieve a localization marker success rate of more than 99.5% using 62 coincidence lines from each marker and an initial error of 10 mm or less. In addition, most of the failed markers may be automatically identified. In one embodiment the number of coincidence lines may be obtained within 100 ms with a 100 μCi marker in a 30 cm thick patient. Referring to FIG. 11A, required marker activity at the time of implantation is depicted in graph 1100, assuming 100 μCi should remain at the end of radiation therapy treatment. Referring to FIG. 11B, graph 1105 shows the life-time dose at 1 cm from the marker may increase with the duration of the treatment according to one or more aspects of the invention. The total time duration may include the time from marker implantation to the first treatment. The isotope and activity may be selected based on the duration of the treatment. Isotopes $^{124}$I, $^{74}$As, and $^{84}$Rb may be selected for a treatment for one of less than 5 days, 5-30 days, and longer than 30 days. According to one aspect of the invention, if the treatment duration is 20 days, markers with 300 μCi $^{74}$As may be used, and the dose at 1 cm from the marker would be 7.5 Gy. If the treatment duration is 30 days, markers with 300 μCi $^{84}$Rb may be used, and the dose at 1 cm from the marker would be 12.5 Gy. The results depicted in FIG. 11 may be based on a 100 μCi/marker minimum activity. This activity may be required for a patient with full 30 cm diameter of tissue which may be appropriately chosen according to patient thickness. Tracking a tumor in the lung or a thin patient will require much lower activity because of reduced patient attenuation. For example, 30 µCi/marker will be enough for a 20 cm diameter patient, which will deliver only ⅓ of the dose shown in FIG. 11.

In another embodiment of the invention, linac induced background estimation may be determined. Table 4 provides the estimation of the random coincidence rate in two pairs of 16×16 cm² tumor tracking detectors from an induced background radiation after delivering 1000 MU with an 18 MV photon beam. Most of the background counts from $^{28}$Al may be assumed to be eliminated by the energy window. The random coincidence rate may be estimated from $^{62}$Cu and $^{187}$W background using equation 8, assuming a 10 ns coincidence time window. The random coincidence rate is 360/sec (see Table 4). This background may be non-negligible compared to the true event rate of ~3000/sec with three 100 µCi markers and a 30 cm patient diameter. Induced radiation background from a 10 MV beam may be only 2.4-7.5% of that from an 18 MV beam, which generates a random coincidence of less than 1 count/sec.

According another embodiment of the invention, radiation damage of a BGO crystal may be determined. An average dose rate may be utilized which may be approximately 140 mR per 300 MU delivered and varied by only a few mR at the two different locations and beam energies. This value represents the dose from the photon background. With a known neutron quality factor of approximately 10, the absorbed dose due to the neutron background component may be estimated to be about ⅒ of those from the photon background according to one embodiment of the invention. Assuming 1000 MU/patient and 35 patients/day in a normal clinical operation, the BGO crystal may accumulate about 0.22 Gy in one day. Doped BGO may show a reduction in light output after 10 to 100 Gy of radiation. However, pure BGO crystals have a much higher radiation resistance from 100 kGy to 1000 kGy, which is sufficiently high to be used for tumor tracking detectors. Furthermore, no after glow was observed on a pure BGO crystal.

According to another aspect of the invention, the success rate of multiple marker localization may depend on the initial estimate of marker positions. Better initial estimates may reduce the number of coincidence-lines required and improve the success rate. However, in a clinical setup, it may not be easy to obtain good initial estimates of implanted marker locations due one of patient setup error and respiratory motion. This problem may be addressed using the following automatic initialization strategy. According to one aspect of the invention, the center of mass of the markers may be determined first by running the localization algorithm assuming only one marker (K=1). The position of each marker may then be initially estimated using a priori knowledge of the relative position of the markers to the center of mass. The a priori knowledge of relative marker positions may be obtained from a post-implantation CT scan. Since a post-implantation CT scan is usually obtained for treatment planning, the patient may not be subjected to an additional procedure apart from the marker implantation. If a tumor shape changes or the markers migrate during radiation therapy treatments, the location information at the end of the previous treatment fraction may be used to localize the initial positions of the individual markers. As described above, a total of 98.3% of the cases may have at least 2 markers located correctly in the first localization attempt. Failed markers may be identified by the value of its cluster standard deviation $\sigma_k$. The positions of the failed markers may be improved by using the known position of the center of mass and successful markers, according to one or more aspects of the invention. The localization may be repeated until all the markers are localized successfully.

In one embodiment of the invention, after successful initial localization, the initial estimation error for subsequent tracking may be equal to the tumor motion during the position sampling interval. At a sampling rate of 10 Hz or time of 100 ms, the tumor motion may be expected to be less than 5 mm. As described above with reference to FIG. 7, in graph 705 with an initial error of ±5 mm, markers may be localized correctly 99.9% of the time with an average of 62 coincidence lines per marker. Therefore, once the initialization is successful, the markers may be accurately tracked throughout the treatment.

Referring to the effect of brachytherapy seeds, some patients may be treated with external beam radiation therapy and implanted brachytherapy seeds, according to one embodiment of the invention. Most of their x-ray and gamma energy may be less than 100 keV and can be easily rejected by the tumor tracking detector through energy discrimination. Thus, the brachytherapy seeds may not affect the performance of the tumor tracking system.

Referring to Table 5, a comparison of the positron emission tumor tracking system with other existing real-time tumor tracking techniques is provided.

TABLE 5

|  | Tracking techniques | | |
|---|---|---|---|
|  | X-ray fluoroscopy | Electro-magnetic technique | Tumor tracking |
| Implanted marker | Gold fiducial | Wireless electro-magnetic transponder | Short half-life positron source 30-300 µCi |
| Marker size | 1.5~2.0 mm diameter sphere | 1.8 mm diameter × 8 mm long cylinder | 0.5~0.8 mm diameter × 2-4 mm length |
| Localization accuracy | 0.5 mm | 0.03~0.2 mm (center of the field) | 0.55(±0.27) mm with 62 coincidence lines per marker |
| Patient dose | 0.3-12 Gy skin dose per hour of treatment time over an area of 200 cm² | 0.0 | ~0.5-17 Gy life-time dose to 4-12 cm³ of tissue |

As shown in Table 5, a major disadvantage of current existing technique is the large size of the marker (1.5 mm~2 mm in diameter). Because of the high frequency of pneumothorax, it may not be recommended to implant such large markers into the lung through the skin surface. These markers may be inserted into the lung using bronchoscopy, which limits the technique to peripheral lung tumors.

In one embodiment of the invention, the size of a tumor tracking marker may be less than half of conventional markers. In one embodiment, markers may have a 0.8 mm outside diameter and 0.6 mm active core corresponding to a standard configuration of brachytherapy seeds. For example, current brachytherapy seeds fabrication technique can produce $^{125}$I seeds with a maximum of 40 mCi concentrated in five 0.6 mm resin spheres (Nycomed-Amersham model 6702). Assuming the positron emission isotopes have the same activity concentration as that of $^{125}$I, a 0.3 mm sphere core may provide 1 mCi activity. Thus, the outside diameter of the tumor tracking marker may be further reduced to 0.5 mm. Due to their smaller size as compared with existing techniques, positron emission markers may be implanted through the skin using a biopsy needle. The smaller size of tumor tracking markers may facilitate implantation and significantly reduce patient risk.

Compared to the existing x-ray fluoroscopy technique, the positron emission tumor tracking technique according to one aspect of the invention, may deliver a much lower dose to the normal tissue when the total time of exposure and affected volume are taken into account. In one embodiment, tumor tracking markers may be implanted into the tumor, which will further reduce its radiation dose to normal tissue, through a biopsy needle. The dose to the tumor resulting from the implanted the markers may be taken into consideration during treatment planning.

Figure 12:
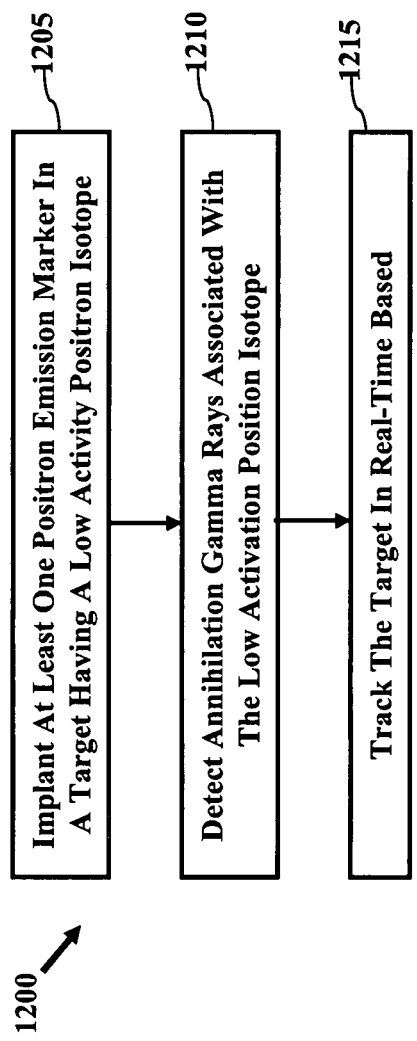
FIG. 12 depicts a process for real-time tracking of a target in a human body, according to one or more aspects of the invention.

Referring now to FIG. 12, a process 1200 is depicted for real-time tracking of a target in a human body, according to one or more aspects of the invention. In one embodiment, process 1200 may be initiated by implanting at least one positron emission marker having a low activity positron isotope in a target as depicted in act 1205. Process may continue with detection of annihilation gamma rays associated with the low activity positron isotope using a plurality of position-sensitive detectors as depicted in act 1210. In one embodiment of the invention, process 1200 may continue with tracking of the target in real-time based on a position of the positron emission marker as illustrated in act 1215.

It should further be appreciated that the principles of the invention may similarly be applied to instrument/tool tracking for surgery and interventional procedures. Positron emission markers, which are much smaller than current electromagnetic markers, may be attached to the instruments or tools. The detectors of the invention (e.g., tracking detectors 105a-d) may detect the annihilate gamma rays from the marker and determine the position of a target instrument or tool with an accuracy of within 1.0 mm, in accordance with one embodiment.

In another embodiment, the invention may determine not only the position, but also an orientation for the target instrument or tool. In such an embodiment, two or three markers with different positron emission isotopes can be attached to the instrument/tool with known relative position. By way of a non-limiting example, Na-22 emits a positron companied by a 1.2 MeV gamma ray, Rb-84 has a 881 keV accompanying gamma ray, and Ge-68 emits positrons without any accompanying gamma ray. Thus, these three different markers may be identified by whether or not they have an accompanying gammas and/or the energy of the accompanying gamma rays (if any). By knowing the spatial location of all the markers, the orientation of the instrument or tool may correspondingly be determined. In one embodiment, the possible positron emission isotopes include I-124, As-74, Rb-84, Na-22, Al-26, Ge-68, V-48 and Co-58.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Trademarks and copyrights referred to herein are the property of their respective owners.

What is claimed is:

1. A method for real-time tracking of a target in a human body, the method comprising the acts of:

implanting into the target a plurality of physical positron emission fiducial markers having a low activity positron-emitting isotope source;

detecting two annihilation gamma rays resulting from positron annihilation associated with each of a plurality of position-emitting nuclear decay events of the low activity positron-emitting isotope source using a plurality of position-sensitive detectors, wherein the plurality of position-sensitive detectors comprises two pairs of position-sensitive detector modules mounted external to the human body in an orthogonal orientation such that the angle between the two pairs of position-sensitive detector modules is between 65 degrees and 90 degrees;

forming a coincident line from only the two detected annihilation gamma rays for each of the plurality of position-emitting nuclear decay events;

sorting the coincident lines into clusters based on an iterative Expectation-Maximization clustering algorithm;

determining the locations of the plurality of physical position emission fiducial markers using only said clusters; and tracking, during radiation therapy delivery, movement and change of orientation of the target in real-time based on a change in position and orientation of plurality of physical positron emission fiducial markers, wherein said tracking provides target movement information for use in performing said radiation therapy delivery.

2. The method of claim 1, wherein said tracking comprising tracking movement and change of orientation of the target in real-time without reconstructing a radioactive distribution image.

3. The method of claim 1, further comprising:
gating off the plurality of position-sensitive detectors during therapy x-ray pulses, and
acquiring positron emission data from the plurality of physical positron emission fiducial markers between said therapy x-ray pulses.

4. The method of claim 1, wherein tracking in real-time comprises tracking the movement and change of orientation of the target at a sampling rate of at least 10 samples per second.

5. The method of claim 1, wherein tracking, during radiation therapy delivery, movement and change of orientation of the target in real-time based on a change in position and orientation of the plurality of physical positron emission fiducial markers, wherein said tracking provides target movement information for use in performing said radiation therapy delivery 6. The method of claim 1, wherein identifying the location comprises identifying a location of the positron emission marker using each of said coincident line clusters with no more than a 100 ms delay.

7. The method of claim 1, wherein said tracking further comprises tracking the target with sub-millimeter accuracy.

8. The method of claim 1, wherein said low activity positron isotope is selected from the list consisting of: I-124, As-74, Rb-84, Na-22, Al-26, Ge-68, V-48 and Co-58.

9. The method of claim 1, wherein implanting comprises one of implanting the positron emission marker in the target or attaching the positron emission marker to the target.

10. The method of claim 1, wherein implanting comprises implanting a plurality of metallic positron emission fiducial markers having a low activity positron isotope into the target, wherein the plurality of metallic positron emission fiducial markers each comprise a radioactive core inside a metallic capsule.

11. A system for radiation therapy based on real-time three-dimensional position and orientation of a target in a human body, comprising:
- a plurality of physical positron emission fiducial markers implanted into the target, the plurality of physical positron emission fiducial markers having a low activity positron-emitting isotope source;
- a plurality of detectors arranged near a radiation isocenter configured to detect two annihilation gamma rays resulting from position annihilation associated with each of a plurality if positron-emitting nuclear decay events of the low activity positron-emitting isotope source of the plurality of physical positron emission fiducial markers, wherein the plurality of position-sensitive detectors comprises two pairs of position-sensitive detector modules mounted external to the human body in an orthogonal orientation such that the angle between the two pairs of position-sensitive detector modules is between 65 degrees and 90 degrees; and
- a module configured to:
  - form a coincident line from only the two detected annihilation gamma rays for each of the plurality of position-emitting nuclear decay events,
  - sort the coincident lines into clusters based on an iterative Expectation-Maximization clustering algorithm,
  - determine the location of one of the plurality of physical position emission fiducial markers using only said clusters, and
  - track, during radiation therapy delivery, movement and change of orientation of the target in real-time based on a change in position and orientation of the plurality of physical positron emission fiducial markers, wherein said module provides target movement information for use in performing said radiation therapy delivery.

12. The system of claim 11, wherein the module is configured to track movement and change of orientation of the target in real-time without reconstructing a radioactive distribution image.

13. The system of claim 11, wherein the module is further configured to gate off the plurality of position-sensitive detectors during therapy x-ray pulses, and to acquire positron emission data from the plurality of physical positron emission fiducial markers between said therapy x-ray pulses.

14. The system of claim 11, wherein the module is configured to track in real-time the movement and change of orientation of the target at a sampling rate of at least 10 samples per second.

15. The system of claim 11, wherein the module is configured to track, during radiation therapy delivery, movement and change of orientation of the target in real-time based on a change in position and orientation of the plurality of physical positron emission fiducial markers, wherein the module is further to provide target movement information for use in performing said radiation therapy delivery.

16. The system of claim 11, wherein the module is configured to identify the location of the positron emission marker using each of said coincident line clusters with no more than a 100 ms delay.

17. The system of claim 11, wherein the module is configured to track the target with sub-millimeter accuracy.

18. The system of claim 11, wherein said low activity positron isotope is selected from the list consisting of: I-124, As-74, Rb-84, Na-22, Al-26, Ge-68, V-48 and Co-58.

19. The system of claim 11, wherein the plurality of physical positron emission fiducial markers are implanted in or attached to the target.

20. The system of claim 11, wherein the plurality of physical positron emission fiducial markers comprise a radioactive core inside a metallic capsule.

21. The system of claim 20, wherein the metallic capsule has an outside diameter of between 0.5 mm and 0.8 mm.

* * * * *